US009543137B2

(12) United States Patent
Apffel et al.

(10) Patent No.: US 9,543,137 B2
(45) Date of Patent: Jan. 10, 2017

(54) SAMPLE DROPLET GENERATION FROM SEGMENTED FLUID FLOW AND RELATED DEVICES AND METHODS

(71) Applicant: Agilent Technologies, Inc., Santa Clara, CA (US)

(72) Inventors: James Alexander Apffel, Mountain View, CA (US); Arthur Schleifer, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/883,990

(22) Filed: Oct. 15, 2015

(65) Prior Publication Data

US 2016/0172178 A1    Jun. 16, 2016

Related U.S. Application Data

(60) Provisional application No. 62/091,243, filed on Dec. 12, 2014.

(51) Int. Cl.
| | | |
|---|---|---|
| *H01J 49/00* | (2006.01) | |
| *H01J 49/10* | (2006.01) | |
| *G01N 21/66* | (2006.01) | |
| *H01J 49/04* | (2006.01) | |
| *G01N 1/44* | (2006.01) | |
| *G01N 35/08* | (2006.01) | |

(52) U.S. Cl.
CPC .............. *H01J 49/10* (2013.01); *G01N 1/44* (2013.01); *G01N 21/66* (2013.01); *G01N 35/08* (2013.01); *G01N 35/085* (2013.01); *H01J 49/0431* (2013.01)

(58) Field of Classification Search
CPC ....... H01J 49/10; H01J 49/0431; G01N 21/66; G01N 1/44
USPC ......................................... 250/281, 282, 288
See application file for complete search history.

(56) References Cited

U.S. PATENT DOCUMENTS

| | | | |
|---|---|---|---|
| 5,504,327 A * | 4/1996 | Sproch ................. | H01J 49/165 250/281 |
| 5,505,832 A * | 4/1996 | Laukien ........... | G01N 27/44717 204/452 |
| 5,993,633 A * | 11/1999 | Smith .............. | G01N 27/44717 204/450 |
| 8,272,576 B2 | 9/2012 | Doak et al. | |
| 8,431,888 B2 | 4/2013 | Kennedy et al. | |
| 2011/0024615 A1 * | 2/2011 | Tanner .................. | G01N 15/10 250/282 |

(Continued)

OTHER PUBLICATIONS

Banerjee, Shibdas, et al, Electrospray Ionization Mass Spectrometry: A Technique to Access the Information Beyond the Molecular Weight of the Analyte, International Journal of Analytical Chemistry, Review Article, Nov. 9, 2011, pp. 1-41, vol. 2012, Article ID 282574, Hindawi Publishing Corporation.

(Continued)

*Primary Examiner* — Michael Maskell (57) ABSTRACT

A sample droplet generator transforms a segmented array of sample material into a continuous stream of droplets containing analytes. The droplets may serve as a sample source for a wide range of detectors and analytical instruments. As one example, the droplets may be introduced into an ion source of a spectrometer that measures ions produced from the droplets or photons emitted from the droplets.

20 Claims, 4 Drawing Sheets

(56) References Cited

U.S. PATENT DOCUMENTS

2012/0153143 A1* 6/2012 Kennedy .............. H01J 49/165
250/282

OTHER PUBLICATIONS

Kuster, Simon K., et al, High-Resolution Droplet-Based Fractionation of Nano-LC Separations onto Microarrays for MALDI-MS Analysis, Analytical Chemistry, American Chemical Society, Apr. 11, 2014, pp. 4848-4855, vol. 86, ACS Publications.

Li, Qiang, et al, Fraction Collection from Capillary Liquid Chromatography and Off-line Electrospray Ionization Mass Spectrometry Using Oil Segmented Flow, NIH Public Access, Author Manuscript, Analytical Chemistry, Jun. 15, 2010, pp. 5260-5267, vol. 82(12).

Lu, Xiaohui, et al, A simplified electrospray ionization source based on electrostatic field induction for mass spectrometric analysis of droplet samples, The Royal Society of Chemistry, 2012, pp. 5743-5748, vol. 137.

Nie, Jing, et al, Capillary liquid chromatography fraction collection and postcolumn reaction using segmented flow microfluidics, Journal of Separation Science, 2013, pp. 3471-3477, vol. 36, Wiley-VCH Verlag GmbH & Co.

Pei, Jian, et al, Rapid Analysis of Samples Stored as Individual Plugs in a Capillary by Electrospray Ionization Mass Spectrometry, NIH Public Access, Author Manuscript, Analytical Chemistry, Aug. 1, 2009, pp. 6558-6561, vol. 81 (15).

Pei, Jian, et al, Rapid and Label-Free Screening of Enzyme Inhibitors Using Segmented Flow Electrospray Ionization Mass Spectrometry, American Society for Mass Spectrometry, 2010, pp. 1107-1113, Elsevier, Inc.

Schneider, Thomas, et al, The Potential Impact of Droplet Microfluidics in Biology, Analytical Chemistry, American Chemical Society, 2013, pp. 3476-3482, vol. 85, ACS Publications.

Silvestre, Cristina I., et al, Liquid-liquid extraction in flow analysis: A critical review, Analytica Chimica Acta, 2009, pp. 54-65, vol. 652, Elsevier B.V.

Su, Yuan, et al, A multifunctional microfluidic droplet-array chip for analysis by electrospray ionization mass spectrometry, Lab on a Chip, The Royal Society of Chemistry, 2013, pp. 1876-1882, vol. 13, RSC Publishing.

Sun, Shuwen, et al, Label Free Screening of Enzyme Inhibitors at Femtomole Scale Using Segmented Flow Electrospray Ionization Mass Spectrometry, Analytical Chemistry, American Chemistry Society, 2012, pp. 5794-5800, vol. 84, ACS Publications.

Sun, Shuwen, et al, Droplet Electrospray Ionization Mass Spectrometry for High Throughput Screening for Enzyme Inhibitors, Analytical Chemistry, American Chemistry Society, 2014, pp. A-F, ACS Publications.

Verboket, Pascal E., et al, A New Microfluidics-Based Droplet Dispenser for ICPMS, Analytical Chemistry, American Chemistry Society, 2014, pp. 6012-6018, vol. 86, ACS Publications.

Volny, Michael, et al, Nanoliter Segmented-Flow Sampling Mass Spectrometry with Online Compartmentalization, Analytical Chemistry, American Chemistry Society, 2014, pp. 3647-3652, vol. 86, ACS Publications.

Wong, Song-Yi, et al., Droplet-based electrospray ionization mass spectrometry for qualitative and quantitative analysis, JMS Letters, Journal of Mass Spectrometry, 2014, pp. 432-436, vol. 49, John Wiley & Sons, Ltd.

Zhu, Ying, et al, Integrated Droplet Analysis System with Electrospray Ionization-Mass Spectrometry Using a Hydrophilic Tongue-Based Droplet Extraction Interface, Analytical Chemistry, American Chemical Society, Oct. 1, 2010, pp. 8361-8366, vol. 82, No. 19.

* cited by examiner

SAMPLE DROPLET GENERATION FROM SEGMENTED FLUID FLOW AND RELATED DEVICES AND METHODS

RELATED APPLICATIONS

This application claims the benefit of U.S. Provisional Patent Application Ser. No. 62/091,243, filed Dec. 12, 2014, titled "SAMPLE DROPLET GENERATION FROM SEGMENTED FLUID FLOW AND RELATED DEVICES AND METHODS," the content of which is incorporated by reference herein in its entirety.

TECHNICAL FIELD

The present invention relates generally to generation of a discontinuous or segmented fluid flow containing sample material, and generation of a stream of sample droplets from the segmented fluid flow. The droplets may be introduced into an analytical instrument for analysis.

BACKGROUND

In the course of various assays and analyses, sample material may be segmented into discrete plugs (or droplets) of fluid spatially separated from each other by a different type of fluid that is immiscible with the sample-containing plugs. For example, the sample plugs may be aqueous while the other fluid utilized to isolate the sample plugs may be organic. Known phase segmenting devices are capable of receiving flows of sample material and isolating material and forming a linear (one-dimensional) array of sample plugs alternately separated by non-sample plugs (or isolator plugs). If the bore of a conduit is small enough (e.g., a capillary tube or microfluidic channel), a linear, segmented sample array can be transported through the conduit to a desired destination, such as a detector or an analytical instrument, while preserving the alternating sequence of sample plugs and non-sample plugs.

In various applications, segmented sample arrays can provide a number of advantages. Each sample plug may serve as an individual medium for transporting the sample material contained therein, with limited or no loss of sample material to the surrounding immiscible phase. Moreover, each sample plug may serve as a self-contained reactor that is isolated from other sample plugs, thus reducing the risk of cross-contamination and enabling different reactions to be carried out in different sample plugs. Moreover, the use of sample plugs can minimize the total volume of sample, reagents, and other material required for a given experiment. Further, the large surface area to volume ratio of sample plugs enables rapid heat transfer (heating or cooling of the sample material).

Segmented sample arrays may potentially be utilized in a wide range of sample processing applications. Applications include, for example, liquid-liquid extraction (LLE) (see, e.g., Silvestre et al., Liquid-liquid extraction in flow analysis: A critical review, Analytica Chimica Acta, 652, 54-65 (2009)), post-chromatography column reaction chemistry (see, e.g., Nie et al., Capillary liquid chromatography fraction collection and postcolumn reaction using segmented flow microfluidics, J. Sep. Sci., 36, 3471-3477 (2013)), and a wide range of droplet-based microfluidic and lab-on-a-chip applications (see, e.g., Schneider et al., The Potential Impact of Droplet Microfluidics in Biology, Anal. Chem., 85, 3476-3482 (2013)).

Segmented flow systems may be interfaced to detectors and analytical instruments. Of recent interest is the injection of segmented sample arrays into electrospray ionization-mass spectrometry (ESI-MS) systems, as segmented sample arrays can potentially meet the sensitivity and time-scale requirements of ESI-MS and MS is a label-free analytical technique. Some prior interfaces have relied on the use of phase separators that split the segmented flow into two separate, homogeneous streams of liquid, and then inject the sample-containing stream into the ESI source. See, e.g., Zhu et al., Integrated Droplet Analysis System with Electrospray Ionization-Mass Spectrometry Using a Hydrophilic Tongue-Based Droplet Extraction Interface, Anal. Chem., 82, 8361-8366(2010). However, the phase separation approach may result in dilution and dispersion of the sample, which inhibit the detection capabilities of the ESI-MS system, as well as an excessive flow rate which may reduce ionization efficiency. Another approach has been to pump a segmented sample array directly into the high-voltage tip of an electrospray needle, whereby the electrospray is produced directly from the sample plugs. See, e.g., Pei et al., Rapid Analysis of Samples Stored as Individual Plugs in a Capillary by Electrospray Ionization Mass Spectrometry, Anal. Chem., 81, 6558-6561(2009); U.S. Pat. No. 8,431,888. In this latter approach, the segmented sample array consist of aqueous sample plugs coated with a small amount of oil and separated from each other by air. To be effective, this approach may be limited to the use of air as the isolating medium between sample plugs in order to avoid spraying oil into the ionization chamber. If liquids are used as the isolation medium, maintaining a stable spray when switching from the aqueous segment to the isolation liquid is likely to cause the spray to stop and the liquid exiting from the tip to remain on the tip and inhibit further spray. Moreover, this approach is limited solely to the use of ESI-MS as the detection technique.

There is a need for generating a stream of sample droplets from a segmented fluid flow that does not require or rely directly on the mechanism of electrospray. The sample droplet stream could thereafter be converted into an electrospray if desired, or could serve as the sample source for various other ionization techniques. More generally, the sample droplet stream could be utilized in a wide range of analytical techniques, including those not requiring ionization of the sample material.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a sample introduction device includes: a segmented sample array source configured for flowing a linear segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the segmented sample array source and a first tube outlet, the first tube defining a sample path; and a second tube sur- 
rounding the first tube and comprising a second tube outlet, wherein the second tube defines a gas path between the first tube and the second tube leading to the second tube outlet, and the second tube outlet is positioned such that the sample path merges into the gas path.

According to another embodiment, a sample introduction device includes: a sample container having characteristic dimension effective for maintaining a linear segmented sample array in a linear arrangement, the segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the sample conduit and a first tube outlet, the first tube defining a sample path; and a second tube surrounding the first tube and comprising a second tube outlet, wherein the second tube defines a gas path between the first tube and the second tube leading to the second tube outlet, and the second tube outlet is positioned such that the sample path merges into the gas path.

According to another embodiment, a sample introduction device includes: a segmented array forming device configured for forming a linear segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the segmented array forming device and a first tube outlet, the first tube defining a sample path; and a second tube surrounding the first tube and comprising a second tube outlet, wherein the second tube defines a gas path between the first tube and the second tube leading to the second tube outlet, and the second tube outlet is positioned such that the sample path merges into the gas path.

According to another embodiment, an atmospheric pressure ionization (API) source includes: a sample introduction device according to any of the embodiments disclosed herein; a chamber communicating with the second tube outlet; and an ionization device configured for ionizing analytes from droplets emitted from the second tube outlet into the chamber at atmospheric pressure.

According to another embodiment, a sample analysis system includes: an API source according to any of the embodiments disclosed herein; and an analytical instrument interfaced with the chamber and configured for acquiring data from ions or photons produced by the API source.

According to another embodiment, a sample analysis system includes: a sample introduction device according to any of the embodiments disclosed herein; and an analytical instrument configured for acquiring data from the analytes or from ions or photons produced from the analytes.

According to another embodiment, a method for generating droplets for analysis includes: flowing a linear segmented sample array along a sample path through a first tube and out from a first tube outlet, the linear segmented sample array comprising a plurality of first plugs alternately separated by a plurality of second plugs, wherein the first plugs comprise a first fluid and analytes and the second plugs comprise a second fluid different from the first fluid; flowing a gas along a gas path between the first tube and a second tube surrounding the first tube, and toward a second tube outlet, wherein the sample path merges into the gas path downstream of the first tube outlet such that at least the first plugs are broken into droplets comprising the analytes; and emitting a stream of the droplets from the second tube outlet.

According to another embodiment, a method for ionizing a sample includes: generating droplets according to any of the methods disclosed herein; emitting the droplets into a chamber at about atmospheric pressure; and ionizing the analytes contained in the droplets.

According to another embodiment, a method for analyzing a sample includes: ionizing analytes according to any of the methods disclosed herein; and measuring an attribute of the ions.

According to another embodiment, a method for atomizing a sample includes: generating droplets according to any of the methods disclosed herein; generating plasma; and emitting the droplets into the plasma.

According to another embodiment, a method for analyzing a sample includes: atomizing the sample to produce sample atoms according to any of the methods disclosed herein; and measuring an attribute of the sample atoms or photons emitted from the sample atoms.

According to another embodiment, a method for analyzing a sample includes: producing droplets according to any of the methods disclosed herein; and acquiring data from the analytes contained in the droplets.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic cross-sectional view of the distal section of an example of a sample droplet generator according to some embodiments of the present disclosure.

FIG. 2 is a schematic view of a sample introduction device or system according to some embodiments.

FIG. 3A is a schematic view of an example of a coaxial junction according to some embodiments.

FIG. 3B is a schematic view of an example of a movable aspiration tube and fluid-filled containers according to some embodiments.

FIG. 4 is a schematic view of an example of a sample analysis system according to some embodiments.

DETAILED DESCRIPTION

As used herein, the term "fluid" is used in a general sense to refer to any material that is flowable through a conduit. Thus, the term "fluid" may generally refer to either a liquid or a gas, unless specified otherwise or the context dictates otherwise.

As used herein, the term "liquid" may generally refer to a solution, a suspension, or an emulsion. Solid particles and/or gas bubbles may be present in the liquid.

As used herein, the term "aerosol" generally refers to an assembly of liquid droplets and/or solid particles suspended in a gaseous medium long enough to be observed and measured. The size of aerosol droplets or particles is typically on the order of micrometers (μm). See Kulkarni et al., Aerosol Measurement, $3^{rd}$ ed., John Wiley & Sons, Inc. (2011), p. 821. An aerosol may thus be considered as comprising liquid droplets and/or solid particles and a gas that entrains or carries the liquid droplets and/or solid particles. The term "spray" may refer to an aerosol that is being or has been subjected to a mechanism of propulsion.

As used herein, the term "atomization" refers to the process of breaking molecules down to atoms. As one non-limiting example, "atomizing" a liquid sample may entail nebulizing the liquid sample to form an aerosol, followed by exposing the aerosol to plasma.

As used herein, the term "sample" includes one or more different types of analytes of interest dissolved or otherwise carried in a fluid matrix. The analytes may be metals, other elements, (bio)chemical compounds, biopolymers (e.g., carbohydrates, polynucleotides, proteins, etc.), or biological materials such as whole (intact) biological cells, a lysed or disrupted cell, or intracellular components. The fluid matrix may be or include water and/or other solvents, soluble materials such as salts and/or total dissolved solids (TDS), and may further include other compounds that are not of analytical interest.

As used herein, the term "atmospheric pressure" is not limited to the standard atmospheric pressure of 760 Torr. Thus, "at" atmospheric pressure encompasses "at or around" or "at about" atmospheric pressure.

As used herein, the term "conduit" generally refers to any type of structure enclosing an interior space that defines a repeatable path for fluid to flow from one point (e.g., an inlet of the conduit) to another point (e.g., an outlet of the conduit). A conduit generally includes one or more walls defining a tube or a channel.

In some embodiments, a conduit may have a small bore. A small-bore tube may be referred to herein as a capillary tube, or capillary. A small-bore channel may be referred to herein as a "microfluidic channel" or "microchannel." The cross-section (or flow area) of a small-bore conduit may have a cross-sectional dimension on the order of micrometers (e.g., up to about 1000 μm, or 1 mm) or lower (e.g., nanometers (nm)). For example, the cross-sectional dimension may range from 100 nm to 1000 μm (1 mm). The term "cross-sectional dimension" refers to a type of dimension that is appropriately descriptive for the shape of the cross-section of the conduit—for example, diameter in the case of a circular cross-section, major axis in the case of an elliptical cross-section, or a maximum width or height between two opposing sides in the case of a polygonal cross-section. Additionally, the cross-section of the conduit may have an irregular shape, either deliberately or as a result of the limitations of fabrication techniques. The cross-sectional dimension of an irregularly shaped cross-section may be taken to be the dimension characteristic of a regularly shaped cross-section that the irregularly shaped cross-section most closely approximates (e.g., diameter of a circle, major axis of an ellipse, width or height of a polygon, etc.). Flow rates through a small-bore conduit may be on the order of microliters per minute (μL/min) or nanoliters per minute (nL/min).

A capillary may be formed by any known technique. The capillary may be formed from a variety of materials such as, for example, fused silica, glasses, polymers, and metals.

A microfluidic channel may be formed in a solid body of material. The material may be of the type utilized in various fields of microfabrication such as microfluidics, microelectronics, micro-electromechanical systems (MEMS), and the like. The composition of the material may be one that is utilized in these fields as a semiconductor, electrical insulator or dielectric, vacuum seal, structural layer, or sacrificial layer. The material may thus be composed of, for example, a metalloid (e.g., silicon or germanium), a metalloid alloy (e.g., silicon-germanium), a carbide such as silicon carbide, an inorganic oxide or ceramic (e.g., silicon oxide, titanium oxide, or aluminum oxide), an inorganic nitride or oxynitride (e.g., silicon nitride or silicon oxynitride), various glasses, or various polymers such as polycarbonates (PC), polydimethylsiloxane (PDMS), etc. The solid body of material may initially be provided in the form of, for example, a substrate, a layer disposed on an underlying substrate, a microfluidic chip, a die singulated from a larger wafer of the material, etc.

The channel may be formed in a solid body of material by any technique, now known or later developed in a field of fabrication, which is suitable for the material's composition and the size and aspect ratio (e.g., length:diameter) of the channel. As non-limiting examples, the channel may be formed by an etching technique such as focused ion beam (FIB) etching, deep reactive ion etching (DRIE), soft lithography, or a micromachining technique such as mechanical drilling, laser drilling or ultrasonic milling. Depending on the length and characteristic dimension of the channel to be formed, the etching or micromachining may be done in a manner analogous to forming a vertical or three-dimensional "via" partially into or entirely through the thickness of the material (e.g., a "through-wafer" or "through-substrate" via). Alternatively, an initially open channel or trench may be formed on the surface of a substrate, which is then bonded to another substrate to complete the channel. The other substrate may present a flat surface, or may also include an initially open channel that is aligned with the open channel of the first substrate as part of the bonding process.

Depending on its composition, the material defining the conduit may be inherently chemically inert relative to the fluid flowing through the conduit. Alternatively, the conduit (or at least the inside surface of the conduit) may be deactivated as part of the fabrication process, such as by applying a suitable coating or surface treatment/functionalization so as to render the conduit chemically inert. Moreover, the inside surface of the conduit may be treated or functionalized so as to impart or enhance a property such as, for example, hydrophobicity, hydrophilicity, lipophobicity, lipophilicity, etc., as needed or desirable for a particular application. Coatings and surface treatments/functionalizations for all such purposes are readily appreciated by persons skilled in the art.

In some embodiments, the material forming the conduit is optically transparent for a purpose such as performing an optics-based measurement, performing a sample analysis, detecting or identifying a substance flowing through the channel, enabling a user to observe flows, etc.

Figure 1:
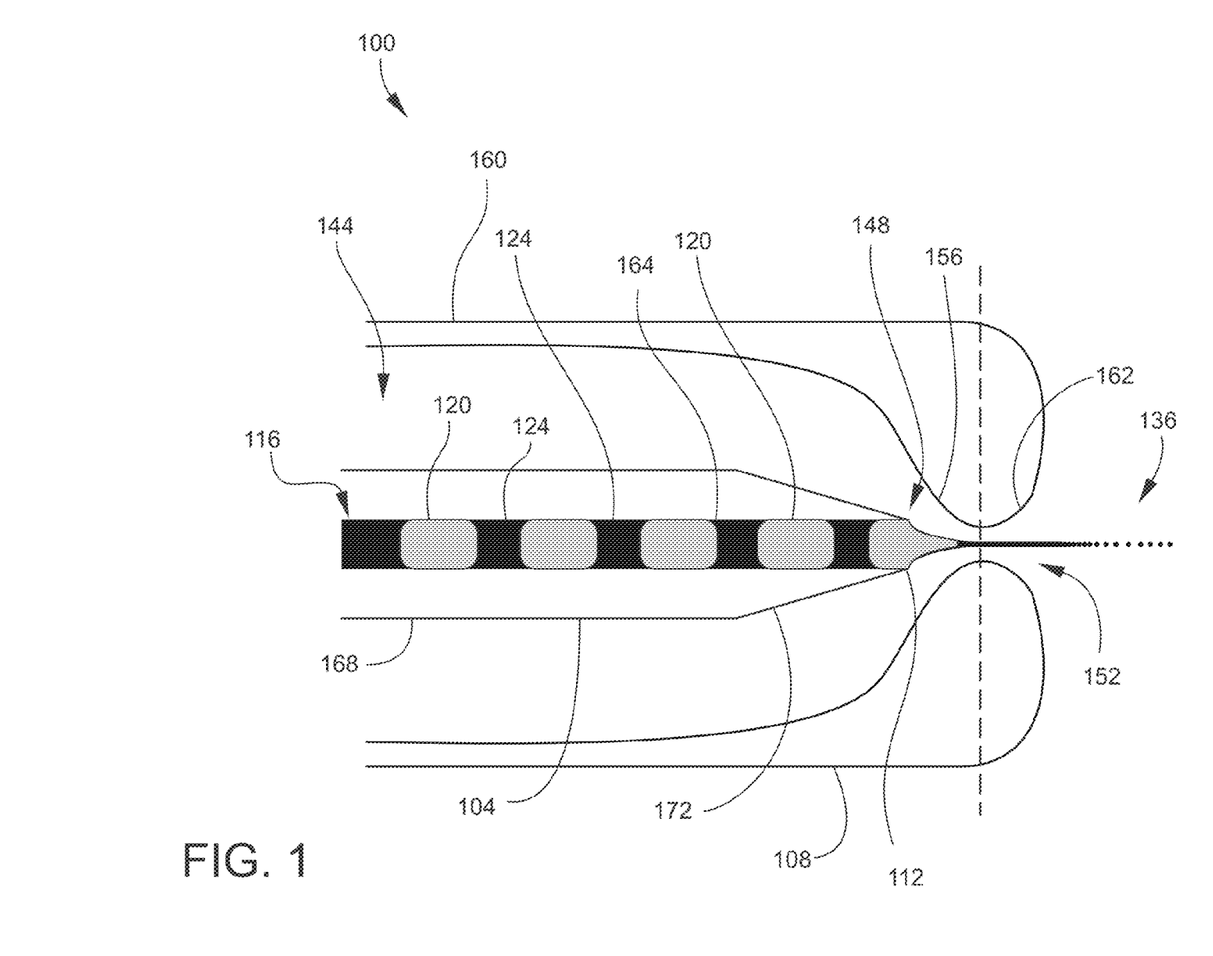

FIG. 1 is a schematic cross-sectional view of the distal (downstream, or tip) section of an example of a sample droplet generator 100 according to some embodiments of the present disclosure. Generally, the sample droplet generator 100 may be any device configured for transforming a segmented (or discontinuous) stream of fluid into a continuous, uninterrupted, stable stream of droplets (aerosol) 136. The segmented fluid stream is introduced into the sample droplet generator 100 as a linear segmented sample array 116. The segmented sample array 116 is arranged as multiple plugs (segments) of sample material, with each plug of sample material being separated from the preceding and succeeding plug of sample material by one or more plugs of different material(s). Generally, a "plug" may also be considered a droplet that is separated by other droplets by an intervening fluid medium of a different material. The segmented sample array 116 may be formed by any suitable method, examples of which are described below. Assuming the flow rates and physical properties of the fluids are compatible with the sample droplet generator 100, the performance of the sample droplet generator 100 may be largely or entirely independent of the means for generating the segmented sample array 116.

In the illustrated embodiment, the segmented sample array 116 includes a plurality of first plugs 120 alternately separated by a plurality of second plugs 124. In some embodiments, the first plugs 120 and the second plugs 124 are substantially immiscible with each other. In other embodiments, depending on the application and the flow rate through the sample droplet generator 100, the first plugs 120 and the second plugs 124 instead may be miscible or partially miscible with each other. The first plugs 120 each include a first fluid and one or more analytes carried (entrained, dissolved, suspended, etc.) in the first fluid. The second plugs 124 each include a second fluid different from the first fluid. Each first plug 120 contacts an adjacent second plug 124 at an interface (boundary) that may be visually distinct. Due to the fluid properties (e.g., surface tension, viscosity, hydrophobicity, hydrophilicity, etc.) of the materials of the first plug 120 and second plug 124, the interface may be curved (convex or concave), as illustrated. In other embodiments, the interface may be more flat.

The first fluid (of the first plugs 120) may be a liquid matrix, such as a solvent or mixture of two or more solvents. The solvent may be water, water with additives, or one or more non-aqueous (organic or inorganic) solvents. In embodiments where the analytes are cells or intracellular components, the first fluid may include intracellular fluid (e.g., cytosol or lysate). Examples of solvents include, but are not limited to, non-polar solvents such as hexane, heptanes, and chloroform; and polar solvents such as alcohols (e.g., methanol, ethanol, isopropyl alcohol, etc.), acetonitrile; tetrahydrofuran (THF); dimethyl sulfoxide (DMSO), and dimethylformamide (DMF). For applications in which the first plugs 120 and the second plugs 124 are immiscible, the second fluid (of the second plugs 124) may be selected based on its effectiveness in maintaining an interface between adjacent pairs of first plugs 120 and second plugs 124, whereby the first plugs 120 remain isolated and spaced from each other while flowing through a conduit. Thus, depending on the nature of the first fluid, the second fluid may be water, or one or more non-aqueous (organic or inorganic) solvents, or one or more oils, silicone oils, or mineral oils suitable for biological applications.

For example, in a case where the first fluid is an aqueous or organic solvent, the second fluid may be an organic compound immiscible with such aqueous or organic solvent. As one example, the second fluid may be a fluorocarbon such as a perfluorinated solvent or a highly fluorinated solvent. Examples of perfluorinated solvents that may be suitable as isolator fluids include, but are not limited to, perfluorodecalin ($C_{10}F_{18}$), and the Fluorinert® fluids commercially available from 3M Company, St. Paul, Minn., USA (e.g., perfluorohexane, or $C_6F_{14}$, designated FC-72 by 3M). Examples of highly fluorinated solvents include fluorinated compounds with properties similar to perfluorinated compounds such as, for example, 1H-perfluorohexane ($C_6HF_{13}$) and perfluorohexyl chloride ($C_6ClF_{13}$).

In other embodiments, the second fluid may be a gas such as oxygen, nitrogen, air, etc.

In other embodiments, more than two different types of plugs may be provided. For example, the segmented sample array 116 may be formed such that each pair of adjacent first plugs 120 is separated by a second plug 124 and a third plug (not shown). The third plug may serve any number of purposes. For example, the third plug may contain a reagent that merges into an adjacent first plug 120 within a microfluidic device as the segmented sample array 116 flows upstream of and/or through the sample droplet generator 100.

The sample droplet generator 100 may be utilized as a sample emitter (sample introduction device) for any detector or analytical instrument requiring a stream or spray of sample droplets 136. In particular, the sample droplet generator 100 may be utilized with an analytical instrument in applications where the analysis is enhanced by the use of a segmented sample array 116 as described above, or further by the use of sample processing done in conjunction with formation of the segmented sample array 116.

The segmented sample array 116 may be formed as part of a wide range of applications. For example, the segmented sample array 116 may be a useful modality for minimizing the amount of sample material required for an analysis. Limiting the analytes to a small volume increases analyte concentration, which can enhance the detection capabilities of certain types of analytical instruments. As one example, spectrometers relying on electrospray ionization (ESI) are sensitive to analyte concentration. The segmented sample array 116 is also useful for transporting analytes in isolation from each other, i.e., with individual analytes encapsulated in respective first plugs 120. Moreover, each first plug 120 may serve as an individual reaction chamber isolated from the other reaction chambers (other first plugs 120). In some applications, different reagents may be added to different first plugs 120 to produce different reactions. As another example, the segmented sample array 116 may be an output from a wide range of microfluidic (or nanofluidic) operations that may be carried out upstream of the sample droplet generator 100. Such upstream operations may be continuous flow-based or droplet-based. Examples of upstream operations for sample preparation or processing include, but are not limited to, analytical separation (or purification, or concentration) such as, for example, liquid chromatography (LC), solid phase extraction (SPE), capillary electrophoresis (CE), liquid-liquid extraction (LLE), dialysis, and techniques based on electrokinesis or electro-osmosis. Further examples of upstream operations include, but are not limited to, reaction, dilution, buffering, pH adjustment, mixing, heating, cooling, incubation, lysis, digestion, valve operation or metering, and pumping.

The sample droplet generator 100 is capable of emitting sample droplets 136 into either an atmospheric pressure environment or a vacuum environment. The sample droplet generator 100 is presently found to be particularly suitable in atmospheric pressure applications. In one particular class of applications, the sample droplet generator 100 may be utilized as a sample emitter in an ion source (particularly an atmospheric pressure ion (API) source) of a spectrometer, such as a mass spectrometer (MS) or an ion mobility spectrometer (IMS). In addition, the sample droplet generator 100 may be utilized as a sample emitter in an analyte photon source such as for an optical emission spectrometer (OES), also referred to as an atomic emission spectrometer (AES). More generally, the sample droplet generator 100 may be utilized as a sample emitter for any detector or analytical instrument capable of receiving a sample in the form of a droplet stream or aerosol.

The sample droplet generator 100 is configured for converting the linear segmented sample array 116 into a stream of droplets 136. In the illustrated embodiment, such configuration is realized as follows. The sample droplet generator 100 includes a central, first tube (or sample tube) 104 defining a first fluid flow path (or sample flow path) for conducting a flow of the segmented sample array 116 along a longitudinal (typically central) axis of the sample droplet generator 100. The sample droplet generator 100 also includes an outer, second tube (nebulizer tube) 108 coaxially surrounding the first tube 104, thereby forming an annular conduit 144 defining a second fluid flow path (or gas flow path) for conducting a flow of nebulizing gas (or "carrier gas"). The first tube 104 terminates at a distal edge 112 that defines a first tube outlet 148 of the first tube 104. The second tube 108 terminates at a second tube outlet (or sample emitter outlet) 152. As illustrated, the first tube 104 and the second tube 108 may be axisymmetric relative to the longitudinal axis. No specification limitation is placed on the materials utilized for fabricating the first tube 104 and the second tube 108. Examples include, but are not limited to, fused silica and various glasses, polymers, and metals.

In some embodiments, the inside diameter of the second tube outlet 152 may be greater than, or at least the same or substantially the same as, the inside diameter of the first tube outlet 148 to help prevent clogging at the outlet 152 due to particles in the liquid stream. In other embodiments, inside diameter of the second tube outlet 152 may be less than the inside diameter of the first tube outlet 148. Generally, the inside diameters of the first tube outlet 148 and the second tube outlet 152, as well as the liquid flow rate and pressure in the first tube 104 and the gas flow rate and pressure in the annular conduit 144, are specified as needed for generating a spray (or aerosol) with a desired size or size distribution of droplets. In some embodiments, the inside diameter of the first tube outlet 148 is in a range from 20 to 100 µm. In some embodiments, the inside diameter of the second tube outlet 152 is in a range from 5 to 100 µm.

The second tube 108 is configured (i.e., the second tube outlet 152 is positioned) such that the sample flow path merges into the gas flow path, whereby the second tube outlet 152 serves as the sole fluid exit (sample emitter outlet) from the sample droplet generator 100. For example, in the illustrated embodiment, this is achieved by configuring the second tube 108 such that the second tube outlet 152 is positioned downstream from the first tube outlet 148, and the first tube outlet 148 is positioned in the distal interior section of the second tube 108. In the illustrated embodiment, the downstream position of the second tube outlet 152 is achieved by forming the second tube 108 to include a converging section 156 at its distal end that transitions down to the second tube outlet 152. That is, the converging section 156 is characterized by the inside diameter (inside surface) of a main portion 160 of the second tube 108 tapering (reducing) down to the inside diameter of the second tube outlet 152. By this configuration, the annular cross-sectional flow area of the gas path transitions to a focused flow area in the space between the first tube outlet 148 and the second tube outlet 152, and the sample flow path is directed into this flow area. By this configuration, the inside diameter of the second tube outlet 152 has a minimum value at the termination of the converging section 156, which is delineated in FIG. 1 by a vertical dashed line.

In some embodiments, as illustrated, the converging section 156 may transition to a diverging section 162—that is, the second tube outlet 152 may be defined by a converging-diverging section. As illustrated, the geometry or profile of the converging section 156 (or the converging section 156 and diverging section 162) may be smooth and rounded and the tapering (change in diameter) relatively gradual. In this case, the converging section 156 (or the converging section 156 and diverging section 162) is free of any sharp edges or abrupt changes in geometry. The length of the converging section 156 and diverging section 162 can be selected for optimum drop generation performance.

In some embodiments, as illustrated, the flow area between the first tube outlet 148 and the second tube outlet 152 is focused along the longitudinal axis of the sample droplet generator 100, with both the first tube outlet 148 and the second tube outlet 152 being coaxial with the longitudinal axis and the second tube outlet 152 being spaced at a downstream axial distance from the first tube outlet 148. In other embodiments, the axis along which the second tube outlet 152 is oriented may be offset from or at an angle to the axis along which the first tube outlet 148 is oriented.

The first tube 104 includes an inside surface 164 defining its inside diameter and an outside surface 168 defining its outside diameter. The inside diameter of the first tube 104 may be constant (straight-walled) up to the distal edge 112 such that it also defines the inside diameter of the first outlet 148. Generally, the inside diameter of the first tube 104 should be sized to maintain the linear arrangement of alternating first plugs 120 and second plugs 124 as they flow through the first tube 104. In some embodiments, the distal edge 112 may be a sharp edge (in other words, the first outlet 148 includes or is defined by a sharp edge). The sharp edge may be characterized as not presenting a flat end face, or as not presenting an appreciable surface area. The sharp edge may also be characterized as an edge at which the inside diameter of the first tube 104 is substantially the same as the outside diameter of the first tube 104. The sharp distal edge 112 eliminates areas where liquid might stagnate, evaporate, and consequently cause accumulation of solid material and eventual clogging. Therefore, the sample droplet generator 100 is highly suitable for the processing of liquid samples containing high concentrations of, for example, dissolved salts and/or TDS.

The sharp distal edge 112 may be formed by any suitable technique, depending on factors such as the size and composition of the first tube 104. Examples include, but are not limited to, grinding and fast ion bombardment (FIB). As illustrated, the sharp distal edge 112 may be formed by beveling or tapering down the distal section of the outside surface 168. That is, the outside surface 168 has a beveled or tapered section 172 along which the outside diameter of the main section of the first tube 104 tapers down to the outside diameter of the sharp distal edge 112—that is, the outside diameter of the first tube 104 reduces down to the sharp distal edge 112. The tapered section 172 may include one bevel or taper angle. Alternatively, the tapered section 172 may include two or more different taper angles, such as smaller-angle bevel that transitions to a greater-angle bevel leading to the sharp distal edge 112. Such a dual- or multiple-bevel configuration may increase the robustness of the first outlet 148 by leaving more material near the sharp distal edge 112.

In operation, a nebulizing (or carrier) gas is flowed through the annular conduit 144 at an appropriate flow rate and pressure, and converges toward the space just downstream from the first tube outlet 148 (between the first tube outlet 148 and the second tube outlet 152). The sample array 116 is flowed through the first tube 104 at an appropriate flow rate and pressure, and exits the first tube outlet 148 as a liquid stream or jet that is coaxially enveloped or sheathed by the gas stream. The sample array 116 is then converted to a stream of droplets 136 containing analyte sample from the first plugs 120. So long as the flow of the sample array 116 is maintained, the stream of droplets 136 will be continuous, uninterrupted, and stable. In some embodiments, the flow of the liquid and the gas may be laminar. In the embodiment specifically illustrated in FIG. 1, the forces exerted by the converging coaxial gas stream may compress the liquid stream of the sample array 116 (i.e., the liquid stream "necks down") to a narrower stream, the diameter of which may be smaller than the (minimum) inside diameter of the second tube outlet 152. This results in the formation of a stream of fine droplets 136 (or microdroplets) containing the analytes of interest. The isolation segments also undergo the same process as the sample segments. As the isolation segment exits the inner liquid capillary at 148, the isolation fluid is compressed by the nebulizing gas and will also form drops at the exit of the drop generator device 100. This is important in that the isolation liquid will not accumulate at the exit of the drop generator exit and stop spraying. Depending on operating conditions, droplets 136 may be formed upstream of the second tube outlet 152, and/or in the second tube outlet 152, and/or just downstream of the second tube outlet 152 (as illustrated). In all such cases, the droplets 136 are characterized herein as being emitted from the second tube outlet 152 of the sample droplet generator 100. The stream of droplets 136 may initially emerge from the second tube outlet 152 as a "single-file" train of droplets (as illustrated). A similar phenomenon has been observed in the context of a gas dynamic virtual nozzle (GDVN). See, e.g., DePonte et al., Gas Dynamic Virtual Nozzle for Generation of Microscopic Droplet Streams, *J. Phys. D: Appl. Phys.* 41 195505 (2008). The train of droplets 136 may shortly thereafter begin to diverge as a generally conical spray.

No specific limitation is placed on the size of the "fine" droplets (or "microdroplets") 136. Generally, the droplets 136 are smaller than the first tube outlet 148 and the second tube outlet 152. As one non-limiting example, the size (diameter) of the droplets 136 may be on the order of micrometers (μm). For example, the size of the droplets 136 may be in a range from hundreds of nanometers to hundreds of micrometers. The size distribution of the droplets 136 may be quite monodisperse.

Figure 2:
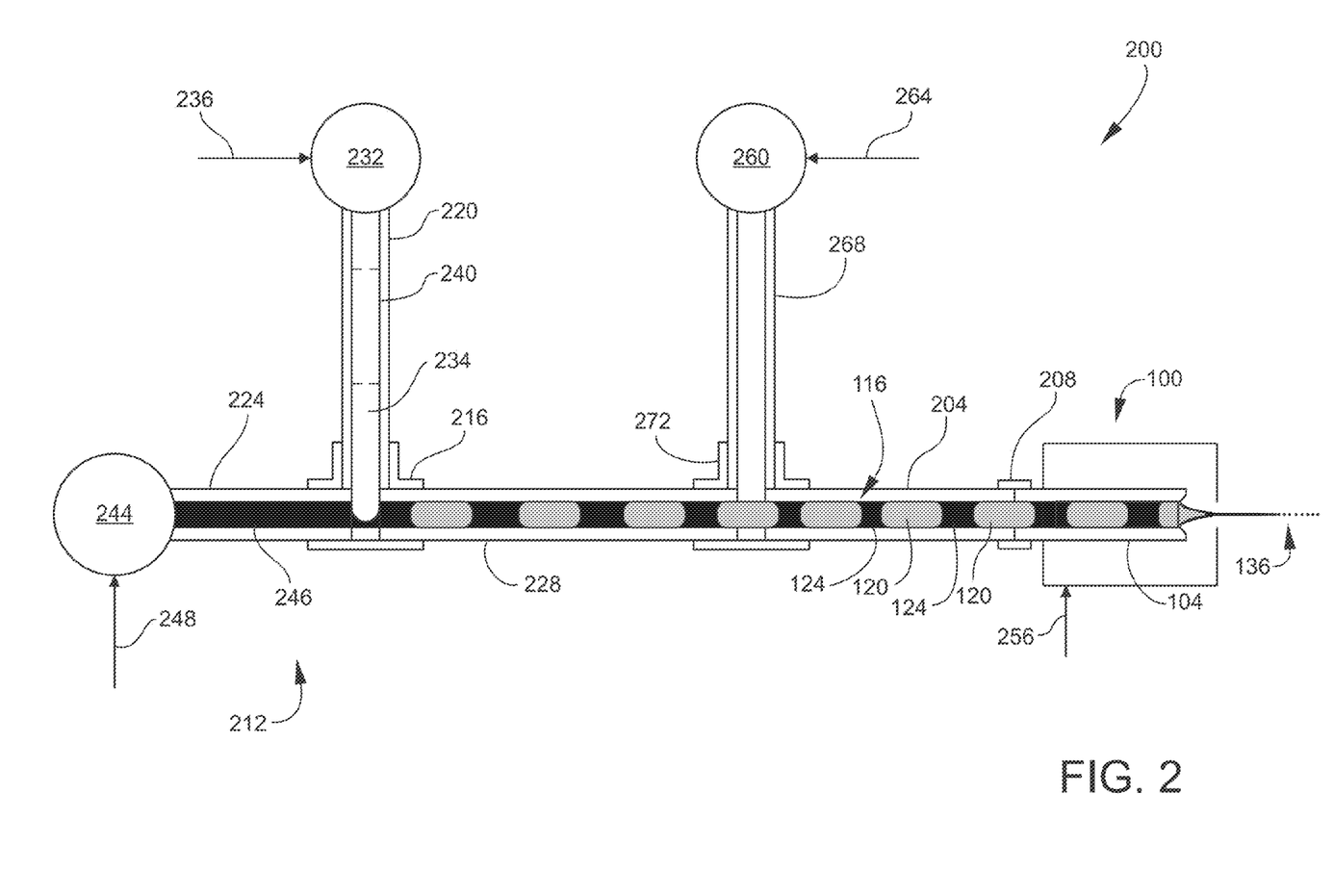

FIG. 2 is a schematic view of a sample introduction device or system 200 according to some embodiments. The sample introduction device 200 may generally include the sample droplet generator 100 and a segmented sample array source communicating with the first tube 104 of the sample droplet generator 100.

In some embodiments, the segmented sample array source may include a sample array container 204. The sample array container 204 is generally configured for containing a sample material as a linear segmented sample array 116 as described above, whereby the segmented sample array 116 may be transported into the first tube 104 by any suitable fluid moving means such as a pump. For this purpose, the sample array container 204 may be a length of a small-bore conduit connected to the first tube 104 by a suitable fluidic coupling. In the illustrated embodiment, the sample array container 204 is a capillary coupled to the first tube 104 by a union 208, for example, a sleeve of material joining the sample array container 204 and the first tube 104 in a fluid-tight manner. Alternatively, the sample array container 204 may be a microfluidic channel coupled to the first tube 104 by a suitable fitting as appreciated by persons skilled in the art.

To establish a flow of the segmented sample array 116 from the sample array container 204 to the first tube 104, a pump may be placed in fluid communication with the sample array container 204, either directly or at an upstream location of a sample supply line of which the segmented sample array 116 forms a part. In the present context, a pump generally may be any device suitable for moving fluids at the flow rates and pressures contemplated for the present subject matter. As examples, a pump may operate on the basis of positive displacement (e.g., a syringe, peristaltic pump, displacement bottle), or another mechanism such as piezoelectric (e.g., driven by a lead zirconate titanate, or PZT, element), ultrasonic, electrostatic, pneumatic, magnetic, hydrodynamic, electro-osmotic, or electrochemical actuation. Moreover, a pump may be adjustable so as to control fluid flow rate (through programming or user interaction), or is understood to operate in conjunction with another component or device configured to control fluid flow rate (e.g., a pressure controller, mass flow controller, flow metering device, valve, etc.). Accordingly, for convenience as used herein the term "pump" as used herein also encompasses any associated flow controlling component that may be provided.

In other embodiments, the segmented sample array source may include a sample array forming device 212. The sample array forming device 212 may communicate with the first tube 104 via the above-described sample array container 204. In such embodiments, the sample array container 204 if also included may be considered as being a conduit of the sample array forming device 212, or as a fluidic interface that couples the sample array forming device 212 to the sample droplet generator 100. Generally, the sample array forming device 212 may have any configuration suitable for generating the linear segmented sample array 116 and transporting the segmented sample array 116 into the sample array container 204 (if provided) and/or the first tube 104.

In some embodiments, the sample array forming device 212 includes a fluidic junction configured for receiving a flow of the first fluid (the precursor for forming first plugs 120) and a flow of the second fluid (the precursor for forming second plugs 124), and for outputting the resulting segmented sample array 116. In the embodiment illustrated in FIG. 2, the fluidic junction is a tee junction 216 communicating with a first supply conduit 220, a second supply conduit 224, and a transfer (or output) conduit 228. A (first) pump 232 transports a first fluid 234 (containing analytes as described above) from a first fluid source 236, through the first supply conduit 220, and to the tee junction 216. The first fluid source 236 may be, for example, a container (reservoir, vial, microplate well, bottle, etc.), a syringe barrel, a sample loop, or an output of a sample processing device (e.g., a device that implements sample preparation, treatment, analytical separation, reaction, dilution, buffering, mixing, heating, cooling, incubation, lysis, digestion, dialysis, filtering, pH adjustment, metering, etc.). In some embodiments, a sample processing device 240 may be integrated with the first supply conduit 220. For example, the sample processing device 240 may be or include a mixing chamber, a reaction chamber, a fluidic coupling communicating with a reagent source (not shown), a stationary phase effective for analytical separation, a dialyzer, a filter or frit, a heat exchanger (e.g., a heating or cooling device), or a combination of two or more of the foregoing. Another (second) pump 244 transports a second fluid 246 (containing media different from the first fluid 234, as described above) from a second fluid source 248, through the second supply conduit 224, and to the tee junction 216. The second fluid source 248 may be, for example, a container (reservoir, vial, microplate well, bottle, etc.), a syringe barrel, a sample loop, etc.

In general operation, the pumps 232 and 244 are operated to establish respective flows of the first fluid 234 and the second fluid 246. The flows are merged in the tee junction 216, resulting in the formation of the segmented sample array 116 of alternating first plugs 120 and second plugs 124. The as-formed segmented sample array 116 is outputted from the tee junction 216 and flows through the transfer conduit 228. The transfer conduit 228 and the sample array container 204 may be the same physical conduit, or may be separate conduits joined by a suitable fluidic coupling. Prior to forming the segmented sample array 116, the system of conduits and other fluidic components may require rinsing and priming as appreciated by persons skilled in the art. In some embodiments, the segmented sample array 116 is formed by controlling the pumps 232 and 244 to control the relative flow rates of the first fluid and the second fluid. In other embodiments, the second pump 244 may be operated to establish a continuous, primary flow of the second fluid 246 into the tee junction 216, while the first pump 232 is operated to precisely inject aliquots of the first fluid 234 into the primary flow according to a desired timing sequence. In this case, the first pump 232 may operate in conjunction with a high-speed fluidic valve or other means as needed to provide the pulsed injection according to the flow injection parameters (amount of the aliquot, pressure, frequency, etc.) required. Alternatively, the first fluid 234 may serve as the continuous, primary flow and the second fluid 246 may be sequentially injected into the first fluid 234.

Figure 3A:
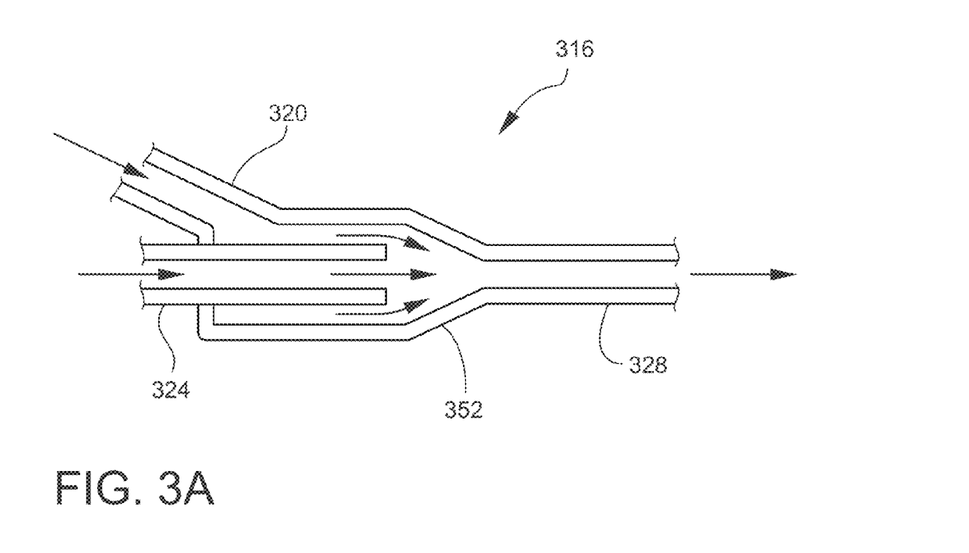

As an alternative to a tee junction, the fluidic junction of the sample array forming device 212 may be a coaxial junction. FIG. 3A is a schematic view of an example of a coaxial junction 316. The coaxial junction 316 includes a merge section (or chamber) 352 that communicates with two supply conduits 320 and 324 and with a transfer (or output) conduit 328. The coaxial junction 316 is configured such that the end of the supply conduit 324 terminates inside the merge section 352, and the fluid flow from the other supply conduit 320 transitions to a coaxial flow surrounding the end region of the supply conduit 324. The two flows merge just downstream of the end of the supply conduit 324, and the resulting or as-forming segmented sample array 116 flows through the transfer conduit 328. Depending on the embodiment, a portion of the supply conduit 320 may be considered as an outer conduit that is part of the merge section 352, and which surrounds the (inner) supply conduit 324. Depending on the embodiment, the supply conduit 320 may introduce the first fluid (for forming first plugs 120) and the other supply conduit 324 may introduce the second fluid (for forming second plugs 124), or vice versa. Moreover, the fluid flow in either supply conduit 320 and 324 may be continuous or pulsed.

In another embodiment, the fluidic junction of the sample array forming device 212 may be a hydrodynamic flow focusing device. Similar to a coaxial junction, a continuous flow of a first fluid is introduced into a continuous flow of a coaxially surrounding, immiscible second fluid. The coaxial fluid streams are then forced through a reduced-diameter orifice in the fluidic junction, whereby the cross-sectional flow area of the first fluid is compressed by the surrounding second fluid, causing the continuous stream of the first fluid to break up into droplets. In still other embodiments, the sample array forming device 212 may include a pneumatic or mechanic injector loop or a non-contact (e.g., magnetic) valve configured to form fluid segments.

Figure 3B:
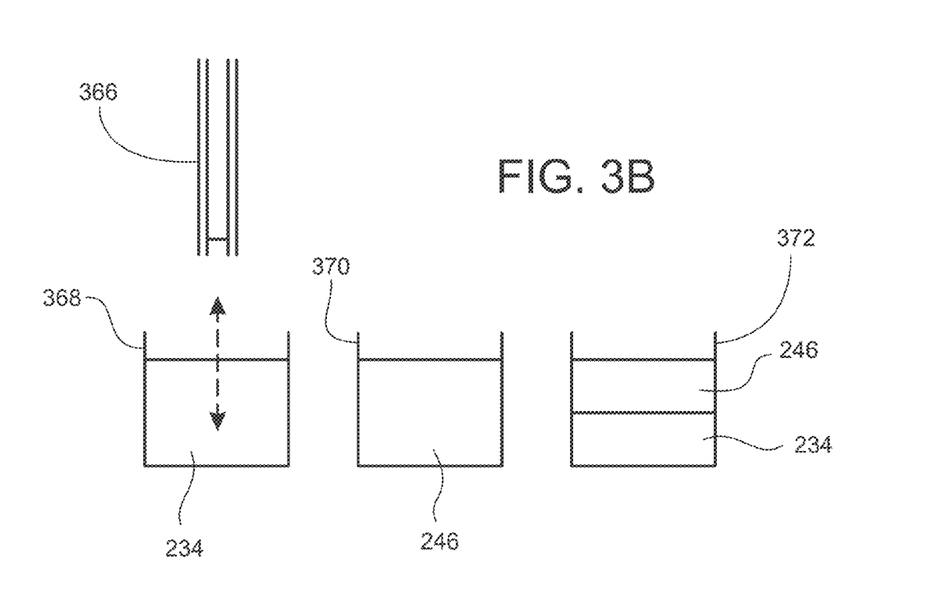

Referring to FIG. 3B, in other embodiments the sample array forming device 212 may include a movable aspiration tube 366 (or sipper tube needle, cannula, etc.). In such embodiments, the sample container 204 (or a conduit upstream of the sample container 204) may be placed in communication with the aspiration tube 366. A pump may be utilized to aspirate fluid into the distal tip of the aspiration tube 366 and push fluid into the sample container 204 (or a conduit upstream thereof) and into the sample droplet generator 100. In a case where air is a suitable medium for isolating sample plugs, the segmented sample array 116 may be formed by alternately inserting the distal tip of the aspiration tube 366 into a container 368 containing the first fluid (and analytes) 234 and removing the aspiration tube 366 from the container 368, according to a desired timing sequence. The pump may be operated during the insertion/removal cycle. In this way, alternating first plugs 120 of the first fluid 234 and second plugs 124 of the second fluid (air) may be formed in the aspiration tube.

In embodiments where the second fluid is a liquid medium, alternating first plugs 120 and second plugs 124 may be formed by alternately dipping the aspiration tube 366 in a first container 368 containing the first fluid 234 and a second container 370 containing the second fluid 246, operating the pump as needed to draw desired amounts of the first fluid 234 and the second fluid 246 during each iteration. Alternatively, the aspiration tube 366 may be pre-filled with one of the fluids, then reciprocated into and out from a container containing the other fluid to aspirate aliquots of the other fluid into the aspiration tube 366. As another alternative in a case where the first fluid 234 and the second fluid 246 are immiscible, both fluids may be initially provided in the same container 372 in which the two fluids form separate layers. In this case, the aspiration tube 366 may be alternately moved (up and down) between a first elevation level at which the distal tip is immersed in the layer containing the first fluid 234, and a second elevation level at which the distal tip is immersed in the layer containing the second fluid 246. In this manner, alternating aliquots of the first fluid 234 and the second fluid 246 may be drawn into the aspiration tube 366.

The foregoing embodiments entailing the use of a movable aspiration tube 366 may require only a single pump and a single sample supply line to the sample droplet generator 100, thereby eliminating the need for separate supply conduits 220 and 224, pumps 232 and 244 (FIG. 2), and a fluidic junction for merging separate flows of the first fluid and the second fluid such as the tee junction 216 (FIG. 2) or coaxial junction 316 (FIG. 3A). Also in the foregoing embodiments entailing the use of an aspiration tube 366, multiple containers may be arranged in a linear or a two-dimensional array. For example, the containers may be the wells of a microplate of standard format. Also in the foregoing embodiments, the manipulations of the aspiration tube 366 may be automated. For example, the aspiration tube 366 may be mounted to a robotic stage such as is commonly part of liquid handling systems, as appreciated by persons skilled in the art.

Referring to FIG. 2, as the segmented sample array 116 is formed it is flowed into the sample droplet generator 100, as well as gas from a gas source 256. The sample droplet generator 100 converts the segmented sample array 116 into droplets 136 as described above, which may be utilized in an ion source or in other types of analytical instruments.

In the foregoing description of the sample introduction device 200 in conjunction with FIGS. 2, 3A and 3B, the formation of the segmented sample array 116 and sample processing are described primarily in the context of an on-line process in which the sample array forming device 212 is coupled to (and thus local to) the sample droplet generator 100. In such on-line configurations, the processes of segmented sample array formation (and any associated sample processing) and sample droplet generation may be carried out simultaneously and in a continuous manner. In other embodiments, the process of forming the segmented sample array 116 may be implemented off-line (and remotely, if desired) relative to the operation of the sample droplet generator 100. As one non-limiting example, a fluid receptacle may be positioned in the place of the sample droplet generator 100 shown in FIG. 2. In this case, the inlet end of the sample container 204 may communicate with the sample array forming device 212 (as described according to any of the foregoing embodiments), and the outlet end of the sample container 204 may communicate with the fluid receptacle. The sample array forming device 212 may then be operated to generate the segmented flow and fill the sample container 204. The sample container 204, now containing the segmented sample array 116, may then be decoupled from the sample array forming device 212, and the open ends of the sample container 204 may then be sealed by any suitable closure mechanisms (e.g., crimping the ends, installing septa or end caps, etc.). Multiple sample containers 204 may be filled in this manner, and stored for a desired period of time under appropriate conditions. Also, multiple sample array forming devices 212 may be utilized to prepare multiple segmented sample arrays 116 in multiple sample containers 204, which may be done in parallel or simultaneously if desired. The filled sample container 204 may thereafter be coupled between the sample droplet generator 100 and an upstream pump and/or associated liquid handling system. Flow of the segmented sample array 116 into the sample droplet generator 100 may then be established, and the sample droplet generator 100 may be operated, as described elsewhere in the present disclosure. Such embodiments allow one analytical instrument to service many sample processing procedures. In addition, some types of sample processing might take a long time to generate the segmented sample stream. In such cases, processing offline frees the analytical instrument for other measurements.

Depending on the application, the first fluid (or the analytes of the first fluid) may be subjected to any processing desired prior to generation of the droplets 136, such as described by example above. Sample processing may be carried out prior to, during, or after formation of the segmented sample array 116. Hence, sample processing may be carried out upstream of, at, or downstream of the sample array forming device 212. As one example, FIG. 2 illustrates the addition of a reagent (or a buffer or other additive) to the segmented sample array 116 at a point after formation of the segmented sample array 116. In the embodiment specifically illustrated, a pump 260 establishes a continuous or pulsed flow of a reagent (or other additive) from a reagent source 264, through a reagent supply conduit 268, and into a tee junction 272 that (in the illustrated example) adjoins the transfer conduit 228 and the sample array container 204. Alternatively or additionally, sample processing may be implemented in the first supply conduit 220 (e.g., at the sample processing device 240) and/or upstream of the first supply conduit 220.

As an example, a reagent may be added to the first fluid to chemically modify the analytes (for example, via derivatization) for various purposes such as, for example, to enhance the detection capabilities of a detector or analytical instrument that receives the droplets 136 from the sample droplet generator 100. As another example, a reagent may be added to carry out postcolumn reaction chemistry on the analytes. As another example, the reagent may be a labeling agent (fluorophore, etc.) added to the analytes to enable any number of different label-dependent analytical/detection techniques downstream of the sample droplet generator 100. In other examples, other types of additives may be added to the first fluid or the second fluid, such as buffers, acids, diluents, pH adjusting agents, surfactants, enzymes, etc. For convenience, the term "reagent" as used herein encompasses any additive that may be added to the first fluid or the second fluid, either before or after segmentation.

In one embodiment, the sample introduction device 200 may be utilized to perform fractionation by carrying out liquid-liquid extraction (LLE) upstream of the sample droplet generator 100 and any detector or analytical instrument receiving the droplet stream 136 from the sample droplet generator 100. Generally, in LLE a feed solution containing a solute (which may be the analyte) to be extracted is contacted with an immiscible solvent. As the feed solution and immiscible solvent flow through an extraction device, the solute is transferred across the interface between the feed solution and the immiscible solvent, thereby enriching the solvent with the solute. In the sample introduction device 200, the sample array forming device 212 may be utilized as the segmentation device for LLE and, with an appropriate length and flow rate, the transfer conduit 228 may be utilized as the extraction device. Either the first fluid or the second fluid serves as the feed solution while the other fluid serves as the receiving solvent. The sample droplet generator 100 is utilized in the place of an LLE phase separator. In operation, the sample array forming device 212 segregates the first fluid and second fluid into first plugs 120 and second plugs 124 as described above. As the resulting segmented sample array 116 flows through the transfer conduit 228, the analyte (or other solute) of each first plug 120 is transferred across the interface with an adjacent second plug 124. This results in the segmented sample array 116 comprising analyte-depleted first plugs 120 (raffinate) and analyte-enriched second plugs 124 (extract). It will be understood that an equivalent reverse extraction process occurs in the case where the second plugs 124 serve as the feed solution and the first plugs 120 serve as the receiving solvent. The LLE-processed segmented sample array 116 may then be flowed directly into the sample droplet generator 100, or stored in the sample container 104 for later injection, as described above.

As an example of an application of LLE in the context of the present disclosure, the extraction of hydrophobic components from an aqueous sample into an organic phase may be performed to simplify complex samples prior to introduction into a mass spectrometer or other analytical instrument. In a specific example, lipids may be extracted from a metabolomic extract to allow enriched analysis of hydrophilic analytes.

More generally, partitioning between adjacent immiscible first plugs 120 and second plugs 124 may be utilized to deliver reagents to the analytes without requiring the use of external reagent injection via a side conduit and tee connection (e.g., the reagent supply conduit 268 and tee junction 272 shown in FIG. 2). For example, the first fluid supplied to the sample array forming device 212 may be an aqueous solution containing analytes, and the second fluid supplied to the sample array forming device 212 may be an organic solvent that includes a reagent. As the segmented sample array 116 flows through the transfer conduit 228, the reagent is transferred from the first plugs 120 to the second plugs 124.

In other embodiments, the first fluid and the second fluid may be miscible or partially miscible to enable various reactions and mixing operations. Flow rates and conduit lengths may be set as needed to carry out the desired reaction or mixing operation. In such embodiments, partial or complete merging of the first plugs 120 and second plugs 124 may occur prior to conversion to droplets 136 by the sample droplet generator 100.

As appreciated by persons skilled in the art, the various conduits and other features of the sample introduction device 200 may be embodied in any combination of capillaries, microfluidic chips, and macro-scale structures.

Figure 4:
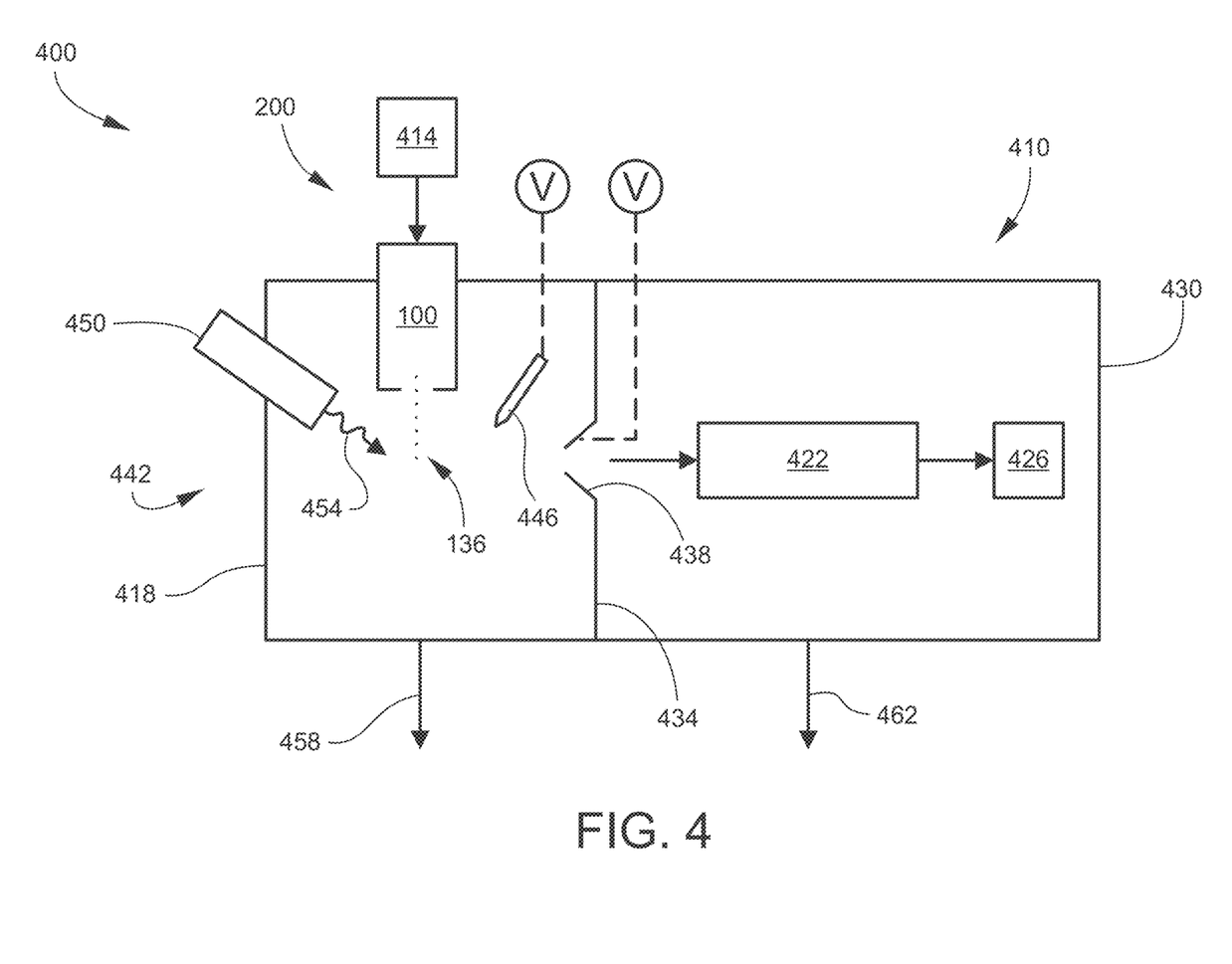

FIG. 4 is a schematic view of an example of a sample analysis system 400 according to some embodiments. The sample analysis system 400 may generally include the sample introduction device or system 200 as described above and an analytical instrument 410. The sample introduction device 200 may generally include the sample droplet generator 100 and a segmented sample array source 414 as described above. Thus, the segmented sample array source 414 may include the sample array container 204 and/or the sample array forming device 212, and the sample introduction device 200 may be operated in an on-line or off-line mode, as described above. The sample droplet generator 100 may communicate with a chamber 418 into which the sample droplet generator 100 emits analyte-containing droplets 136. Depending on the embodiment, the chamber 418 may be considered a part of the analytical instrument 410, or an interface (such as, for example, an atmospheric pressure interface) between the sample introduction device 200 and the analytical instrument 410.

The analytical instrument 410 may generally include an analyzing device 422 and a detector 426, the configuration and operation of which depend on the type of analytical instrument 410 being implemented. Generally, the analyzing device 422 and detector 426 are configured to measure an attribute of (i.e., acquire data from) analytes contained in the droplets 136, or atoms, ions, or photons produced from the analytes. In some embodiments, the analyzing device 422 and detector 426 are located in a housing 430 separated from the chamber 418 by a boundary 434 such as a wall. A sampling interface 438 positioned at or formed through the boundary 434 may define a path for analytes, or ions or photons produced from the analytes (depending on the embodiment), to be transported to the analyzing device 422. In some embodiments, a pressure differential exists between the respective interiors of the chamber 418 and the housing 430. In some embodiments, the interior of the housing 430 is maintained at a vacuum level while the interior of the chamber 418 is maintained at around atmospheric pressure. In some embodiments, the housing 430 includes multiple chambers maintained at different pressures, such as successively reduced pressures in embodiments in which the analyzing device 422 must be operated at a high vacuum level.

In some embodiments, as illustrated, the sample analysis system 400 includes an atmospheric pressure ionization (API) source 442. The API source 442 includes an ionization device configured for producing analyte ions from the analytes contained in the droplets 136 emitted from the sample droplet generator 100. The type of ionization device depends on the type of API source 442 provided. Examples of API sources 442, include, but are not limited to, electrospray ionization (ESI) sources, atmospheric pressure chemical ionization (APCI) sources, atmospheric pressure photoionization (APPI) sources, and inductively coupled plasma (ICP) sources and other plasma-based sources. Ions produced in the API source 442 or photons emitted from atoms produced in the API source 442 are directed into the housing 430 via the sampling interface 438. In some embodiments, a flow of an inert drying gas (e.g., nitrogen, argon, etc.) may be directed into the chamber 418, such as coaxially around the sampling interface 438 or as a curtain in front of the sampling interface 438, to assist in preventing neutral molecules from passing through the sampling interface 438.

In some embodiments, the ionization device may include an electrode 446 communicating with a voltage source. In a case where the API source 442 is configured as an ESI source, the electrode 446 may be positioned to operate in conjunction with an appropriately positioned counter-electrode to produce an electric field having a spatial orientation effective for producing an electrospray from the droplets 136. Analyte ions are consequently produced from the electrospray according to known mechanisms. The electrode 446 may be positioned at a distance from the sample droplet generator 100 or may be in contact with an electrically conductive portion of the sample droplet generator 100. It will be noted, however, that the sample droplet generator 100 generates electrically neutral (non-charged) droplets 136 (in the manner described above in conjunction with FIG. 1) separately and independently of the subsequent generation of electrospray from the droplets 136. The sampling interface 438 (ion inlet), for example, may serve as the counter-electrode.

In other embodiments in which the API source 442 is configured as an APCI source, the electrode 446 may be configured and positioned to generate a corona discharge (i.e., a corona discharge needle) to which the droplets 136 are exposed, as appreciated by persons skilled in the art. The carrier gas emitted from the sample droplet generator 100 may be utilized to form primary ions, or a separate input of a reagent gas (not shown) may be provided for this purpose.

In other embodiments, the ionization device may include a plasma source 450. In the case of APPI, photons 454 generated in the plasma irradiate the droplets 136 to form ions. The photons 454 may propagate through a window of the plasma source 450, or the plasma source 450 may have a windowless configuration as appreciated by persons skilled in the art. The plasma may be generated and sustained by various known techniques. The plasma-forming gas may be a single gas species or a combination or two or more different species. Various types of plasmas, and the design and operating principles of various types of energy sources utilized to generate plasmas, are generally known to persons skilled in the art and thus for purposes of the present disclosure need not be described further.

In other embodiments entailing APPI, a non-plasma based photon source may be utilized instead of the plasma source 450. For example, the photons 454 may be a coherent beam generated by a laser.

In other embodiments entailing plasma-based ionization, the charged species of the plasma (plasma electrons and/or plasma ions) may interact with the droplets 136 to form ions. The plasma source 450 may, for example, be an inductively coupled plasma (ICP) source. In such embodiments, the plasma source 450 may be configured as a plasma torch having a concentric tube configuration, with a sample inlet communicating with the outlet of the sample droplet generator 100 (not specifically shown). The stream of droplets 136 emitted from the sample droplet generator 100 may flow through a central tube of the plasma torch, while a plasma-forming gas flows through an annular conduit coaxial with the flow of droplets 136 and is energized into a plasma. The droplets 135 are then injected into the plasma, and the resulting analytes ions and gases are discharged from an outlet of the plasma torch into the chamber 418.

In embodiments in which analyte ions are measured (e.g., the API source 442 is configured as an ESI, APCI, APPI, or plasma-based source), the analyte ions produced in the API source 442 are directed (under the influence of gas flow, a pressure differential, and/or voltage gradient) into the housing 430 via the sampling interface 438. The sampling interface 438 may include ion optics configured for extracting the analyte ions and transmitting them as a focused beam to the analyzing device 422. Ion optics may include, for example, a skimmer plate as schematically illustrated, a capillary tube, an ion lens, etc. An exhaust port 458 may remove neutral gases from the chamber 418. One or more vacuum ports 462 may remove gases from the housing 430 to maintain the required levels of vacuum in the analyzing section. Additionally, a flow of an inert drying gas (e.g., argon, nitrogen, etc.) may be established (not shown) near the sampling interface 438 to assist in reducing the amount of neutral gas molecules passing into the analyzing section.

In some embodiments in which analyte ions are measured, the analytical instrument 410 may be a mass spectrometer (MS). As appreciated by persons skilled in the art, an MS is configured for receiving analyte ions, spectrally resolving the analyte ions on the basis of their respective mass-to-charge (m/z) ratios, and measuring the ion abundance (counting the ions) of each m/z ratio detected. In such embodiments, the analyzing device 422 is a mass analyzer. The structure and operation of various types of mass analyzers are known to persons skilled in the art. Examples of mass analyzers include, but are not limited to, multipole electrode structures (e.g., quadrupole mass filters, linear ion traps, three-dimensional Paul traps, etc.), time-of-flight (TOF) analyzers, electrostatic traps (e.g. Kingdon, Knight and ORBITRAP® traps) and ion cyclotron resonance (ICR) traps (FT-ICR or FTMS, also known as Penning traps). The detector 426 may be any device configured for collecting and measuring the flux (or current) of mass-discriminated ions outputted from the analyzing device 422. Examples of ion detectors 426 include, but are not limited to, image current detectors, electron multipliers, photomultipliers, Faraday cups, and micro-channel plate (MCP) detectors.

In other embodiments in which analyte ions are measured, the analytical instrument 410 may be an ion mobility spectrometer (IMS). As appreciated by persons skilled in the art, an IMS is configured for receiving analyte ions, spectrally resolving the analyte ions on the basis of their respective ion mobilities (e.g., drift time), and measuring the ion abundance as a function of ion mobility. In such embodiments, the analyzing device 422 is a drift cell, which may be configured for operation at around atmospheric pressure or at vacuum. Ions drift through the drift cell in the presence of an inert buffer gas (e.g., argon, nitrogen, etc.) under the influence of a voltage gradient established along the axial length of the drift cell. The time required for an ion to traverse the length of the drift cell is a measurement of its ion mobility, and is primarily dependent on its collisional cross-section (CCS). In still other embodiments, the analytical instrument 410 may have a hyphenated configuration such as, for example, an IM-MS instrument in which an IM drift cell is followed by a mass analyzer.

In other embodiments in which the API source 442 is configured for plasma-based ionization (e.g., utilizing a plasma torch as the plasma source 450), the photons emitted from analyte atoms produced in the plasma are measured, instead of analyte ions. In such embodiments, the analytical instrument 410 may be an optical emission spectrometer (OES), also referred to as an atomic emission spectrometer (AES). As appreciated by persons skilled in the art, an OES is configured for receiving photons emitted from the sample atoms as they relax from their excited states (induced by the plasma), spectrally resolving the photons on the basis of their respective wavelengths, and measuring the light intensity (abundance) at each wavelength. In the case of OES, the sampling interface 438 may include photon optics (e.g., windows, lenses, mirrors, etc.) for collecting the light emitted from the sample atoms and transmitting the light as a focused beam to the analyzing device 422. The analyzing device 422 may be, for example, a diffraction grating or other device configured for spectrally resolving the different wavelengths of the ensemble of photons comprising the light beam. The detector 426 may be any suitable optical detector such as, for example, one or more photomultiplier tubes (PMTs), photodiodes, charge coupled devices (CCDs), etc.

Analyte-containing droplets 136 generated as described above may be useful in other types of analytical instruments. Thus, in some embodiments the analytical instrument 410 of the sample analysis system 400 may be or include an ultraviolet (UV), visible (Vis), infrared (IR), or Fourier transform infrared (FTIR) spectroscopy instruments, or an instrument that measures light absorbance, light transmission, light scattering, Raman scattering, fluorescence, luminescence, etc., or a microscope or other imaging device. A reagent serving as a labeling agent may be added to the analytes, for example in the context of flash or glow luminescence or fluorescence.

Moreover, the stream of analyte-containing droplets 136 may be utilized to prepare other types of sample formats. For example, the droplets 136 may be dispensed into a container or the well of a microplate. In another example, the analytical instrument 410 may be or include an optical plate reader. As another example, the droplets 136 may be applied as a coating to a substrate, or through a mask to produce a pattern on a substrate, or applied so as to create sample spots on a substrate.

It will also be understood that the sample analysis system 400 may further include a system controller (not shown) that controls and coordinates the various operations of the components of the sample analysis system 400. The system controller may include one or more types of hardware, firmware and/or software, as well as one or more memories and databases, as needed for these purposes.

It will be understood that FIGS. 1 to 4 are high-level schematic depictions of the systems, devices, and features described above. As appreciated by persons skilled in the art, other components such as additional structures, devices, fluidics and electronics may be included as needed for practical implementations, depending on a given application.

Exemplary Embodiments

Exemplary embodiments provided in accordance with the presently disclosed subject matter include, but are not limited to, the following:

1. A sample introduction device, comprising: a segmented sample array source configured for flowing a linear segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the segmented sample array source and a first tube outlet, the first tube defining a sample path; and a second tube surrounding the first tube and comprising a second tube outlet, wherein the second tube defines a gas path between the first tube and the second tube leading to the second tube outlet, and the second tube outlet is positioned such that the sample path merges into the gas path.

2. The sample introduction device of embodiment 1, wherein the segmented sample array source comprises a sample container having a size effective for maintaining the segmented sample array in a linear arrangement.

3. The sample introduction device of embodiment 2, wherein the sample container is removably coupled to the first tube.

4. The sample introduction device of any of embodiments 1 to 3, wherein the segmented sample array source comprises a segmented array forming device.

5. The sample introduction device of embodiment 4, wherein the segmented array forming device comprises a supply conduit for flowing the first fluid from a reservoir.

6. The sample introduction device of embodiment 5, wherein the segmented array forming device comprises a sample processing device communicating with the supply conduit.

7. The sample introduction device of embodiment 6, wherein the sample processing device is selected from the group consisting of: a mixing chamber; a reaction chamber; a fluidic coupling communicating with a reagent source; a stationary phase effective for analytical separation; an analytical separation device; a dialyzer; a filter; a heat exchanger; and a combination of two or more of the foregoing.

8. The sample introduction device of any of embodiments 4 to 7, wherein the segmented array forming device comprises a fluidic junction, a first supply conduit for conducting the first fluid to the fluidic junction, and a second supply conduit for conducting the second fluid to the fluidic junction.

9. The sample introduction device of embodiment 8, wherein the fluidic junction comprises a tee junction, a coaxial junction, a flow focusing device, or a loop injector.

10. The sample introduction device of embodiment 8 or 9, wherein the segmented array forming device comprises a first pump configured for flowing the first fluid to the fluidic junction, and a second pump configured for flowing the second fluid to the fluidic junction.

11. The sample introduction device of embodiment 10, wherein at least one of the first pump and the second pump is configured for flowing the first fluid or the second fluid in a pulsed manner.

12. The sample introduction device of any of embodiments 4 to 11, wherein the segmented array forming device comprises an aspiration tube, and one or more reservoirs containing the first fluid, the second fluid, or both the first fluid and the second fluid, wherein the aspiration tube is selectively movable into the one or more reservoirs.

13. The sample introduction device of any of embodiments 1 to 12, comprising a pump configured for flowing the segmented sample array from the segmented sample array source into the first tube.

14. The sample introduction device of any of embodiments 1 to 13, wherein the second tube outlet has a diameter substantially the same as or greater than an inside diameter of the first tube outlet.

15. The sample introduction device of any of embodiments 1 to 14, wherein the second tube outlet comprises a converging section or a converging-diverging section.

16. The sample introduction device of any of embodiments 1 to 15, wherein the first tube and the second tube extend along a longitudinal axis, and the second tube outlet is positioned at a downstream axial distance from the first tube outlet.

17. The sample introduction device of any of embodiments 1 to 16, comprising an atmospheric pressure chamber communicating with the second tube outlet.

18. A sample introduction device, comprising: a sample container having characteristic dimension effective for maintaining a linear segmented sample array in a linear arrangement, the segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the sample conduit and a first tube outlet, the first tube defining a sample path; and a second tube surrounding the first tube and comprising a second tube outlet, wherein the second tube defines a gas path between the first tube and the second tube leading to the second tube outlet, and the second tube outlet is positioned such that the sample path merges into the gas path.

19. A sample introduction device, comprising: a segmented array forming device configured for forming a linear segmented sample array comprising a plurality of first plugs alternately separated by a plurality of second plugs, wherein the first plugs comprise a first fluid and analytes and the second plugs comprise a second fluid different from the first fluid; and a sample droplet generator configured for generating a stream of droplets from the segmented sample array wherein the droplets comprise the analytes, the sample droplet generator comprising: a first tube comprising a first tube inlet communicating with the segmented array forming device and a first tube outlet, the first tube defining a sample path; and a second tube surrounding the first tube and comprising a second tube outlet, wherein the second tube defines a gas path between the first tube and the second tube leading to the second tube outlet, and the second tube outlet is positioned such that the sample path merges into the gas path.

20. An atmospheric pressure ionization (API) source, comprising: a sample introduction device according to any of embodiments 1 to 19; a chamber communicating with the second tube outlet; and an ionization device configured for ionizing analytes from droplets emitted from the second tube outlet into the chamber at atmospheric pressure.

21. The API source of embodiment 20, wherein the ionization device is selected from the group consisting of: an electrode configured for generating electrospray from the droplets; an electrode configured for generating a corona discharge effective for atmospheric pressure chemical ionization; a photon source; a plasma source; a plasma torch communicating with the second tube outlet; and a combination of two or more of the foregoing.

22. A sample analysis system, comprising: an API source according to embodiment 20 or 21; and an analytical instrument interfaced with the chamber and configured for acquiring data from ions or photons produced by the API source.

23. The sample analysis system of embodiment 22, wherein the analytical instrument is selected from the group consisting of: a mass spectrometer; an ion mobility spectrometer; and an optical emission spectrometer.

24. A sample analysis system, comprising: a sample introduction device according to any of embodiments 1 to 19; and an analytical instrument configured for acquiring data from the analytes or from ions or photons produced from the analytes.

25. The sample analysis system of embodiment 24, comprising a chamber positioned to receive droplets emitted from the sample introduction device, and optics between the chamber and the analytical instrument.

26. A method for generating droplets for analysis, the method comprising: flowing a linear segmented sample array along a sample path through a first tube and out from a first tube outlet, the linear segmented sample array comprising a plurality of first plugs alternately separated by a plurality of second plugs, wherein the first plugs comprise a first fluid and analytes and the second plugs comprise a second fluid different from the first fluid; flowing a gas along a gas path between the first tube and a second tube surrounding the first tube, and toward a second tube outlet, wherein the sample path merges into the gas path downstream of the first tube outlet such that at least the first plugs are broken into droplets comprising the analytes; and emitting a stream of the droplets from the second tube outlet.

27. The method of embodiment 26, wherein the first fluid and second fluid are substantially immiscible.

28. The method of embodiment 26 or 27, wherein one of the first fluid and the second fluid comprises an aqueous medium and other of the first fluid and the second fluid comprises an organic medium.

29. The method of any of embodiments 26 to 28, wherein the first fluid comprises an aqueous medium and the second fluid comprises a fluorocarbon, an oil, or a gas.

30. The method of any of embodiments 26 to 29, comprising emitting the stream of droplets into an environment at around atmospheric pressure.

31. The method of any of embodiments 26 to 30, comprising, before flowing the linear segmented sample array through the first tube, flowing the linear segmented sample array into a sample container.

32. The method of embodiment 31, comprising at least one of: storing the sample container for a period of time; transporting the sample container to the first tube; or coupling the sample container with the first tube.

33. The method of any of embodiments 26 to 32, comprising forming the linear segmented sample array.

34. The method of embodiment 33, comprising, before or after forming the linear segmented sample array, carrying out a sample process on the first fluid selected from the group consisting of: mixing the first fluid with another fluid; adding a reagent to the first fluid; carrying out an analytical separation technique on the first fluid; diluting the first fluid; carrying out dialysis on the first fluid; lysing a cell contained in the first fluid; filtering the first fluid; transferring heat to or from the first fluid; and a combination of two or more of the foregoing.

35. The method of embodiment 33 or 34, wherein forming the linear segmented sample array comprises flowing the first fluid from a reservoir.

36. The method of any of embodiments 33 to 35, wherein forming the linear segmented sample array comprises flowing the first fluid and the second fluid into a fluid junction, and flowing the linear segmented sample array out from the fluid junction.

37. The method of embodiment 36, wherein flowing at least one of the first fluid and the second fluid is done according to a pulse sequence.

38. The method of any of embodiments 33 to 37, wherein forming the linear segmented sample array comprises alternately inserting an aspiration tube into a container and aspirating a quantity of at least one of the first fluid and the second fluid from the container, and removing the aspiration tube from the container.

39. The method of any of embodiments 26 to 38, comprising, before flowing the linear segmented sample array through the first tube, carrying out liquid-liquid extraction on the linear segmented sample array.

40. The method of any of embodiments 26 to 39, wherein the first plugs and the second plugs are immiscible, and further comprising, before flowing the linear segmented sample array through the first tube, flowing the linear segmented sample array through a transfer conduit for a period of time sufficient for a component contained in the first plugs or the second plugs to be transferred into adjacent plugs.

41. The method of any of embodiments 26 to 39, wherein the first plugs and the second plugs are at least partially miscible, further comprising, before flowing the linear segmented sample array through the first tube, flowing the linear segmented sample array through a transfer conduit for a period of time sufficient for the first plugs to at least partially merge with the second plugs.

42. The method of any of embodiments 26 to 41, comprising emitting the droplets into a chamber at about atmospheric pressure.

43. A method for ionizing a sample, the method comprising: generating droplets according to the method of any of embodiments 26 to 42; emitting the droplets into a chamber at about atmospheric pressure; and ionizing the analytes contained in the droplets.

44. The method of embodiment 43, comprising ionizing the analytes by a technique selected from the group consisting of: electrospray ionization (ESI); atmospheric pressure chemical ionization (APCI); atmospheric pressure photoionization (APPI); and plasma-based ionization.

45. A method for analyzing a sample, the method comprising: ionizing analytes according to the method of embodiments 43 or 44; and measuring an attribute of the ions.

46. The method of embodiment 45, wherein measuring an attribute of the ions comprises measuring mass-to-charge ratio, ion mobility, or both mass-to-charge ratio and ion mobility.

47. A method for atomizing a sample, the method comprising: generating droplets according to the method of any of embodiments 26 to 42; generating plasma; and emitting the droplets into the plasma.

48. A method for analyzing a sample, the method comprising: atomizing the sample to produce sample atoms according to the method of embodiment 47; and measuring an attribute of the sample atoms or photons emitted from the sample atoms.

49. A method for analyzing a sample, the method comprising: producing droplets according to the methods any of embodiments 26 to 48; and acquiring data from the analytes contained in the droplets.

50. The method of embodiment 49, wherein acquiring data is selected from the group consisting of: measuring an optical property of the analytes; producing ions from the analytes, and spectrally resolving the ions according to mass-to-charge ratio; producing ions from the analytes, and spectrally resolving the ions according to ion mobility; producing energized atoms from the analytes, and spectrally resolving photons emitted from the atoms according to wavelength; and a combination of two or more of the foregoing.

All references cited herein are incorporated by reference in their entireties.

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample introduction device, comprising:
a segmented sample array source configured for flowing a linear segmented sample array comprising a plurality of first plugs alternately separated by a plurality of second plugs, wherein the first plugs comprise a first fluid and analytes and the second plugs comprise a second fluid different from the first fluid; and
a sample droplet generator configured for generating a stream of droplets from the segmented sample array wherein the droplets comprise the analytes, the sample droplet generator comprising:
a first tube comprising a first tube inlet communicating with the segmented sample array source and a first tube outlet, the first tube defining a sample path; and
a second tube surrounding the first tube and comprising a second tube outlet, wherein the second tube defines a gas path between the first tube and the second tube leading to the second tube outlet, and the second tube outlet is positioned such that the sample path merges into the gas path, and
wherein the first tube and the second tube extend along a longitudinal axis, and the second tube outlet is positioned at a downstream axial distance from the first tube outlet.

2. The sample introduction device of claim 1, wherein the segmented sample array source comprises a sample container having a size effective for maintaining the segmented sample array in a linear arrangement.

3. The sample introduction device of claim 1, wherein the segmented sample array source comprises a segmented array forming device.

4. The sample introduction device of claim 3, wherein the segmented array forming device comprises a feature selected from the group consisting of:
a supply conduit for flowing the first fluid from a reservoir;
a sample processing device communicating with the supply conduit;
a fluidic junction, a first supply conduit for conducting the first fluid to the fluidic junction, and a second supply conduit for conducting the second fluid to the fluidic junction;
a first pump configured for flowing the first fluid, and a second pump configured for flowing the second fluid; and
an aspiration tube, and one or more reservoirs containing the first fluid, the second fluid, or both the first fluid and the second fluid, wherein the aspiration tube is selectively movable into the one or more reservoirs.

5. An atmospheric pressure ionization (API) source, comprising:
the sample introduction device of claim 1;
a chamber communicating with the second tube outlet; and
an ionization device configured for ionizing analytes from droplets emitted from the second tube outlet into the chamber at atmospheric pressure.

6. A sample analysis system, comprising:
the API source of claim 5; and
an analytical instrument interfaced with the chamber and configured for acquiring data from ions or photons produced by the API source.

7. A sample analysis system, comprising:
the sample introduction device of claim 1; and
an analytical instrument configured for acquiring data from the analytes or from ions or photons produced from the analytes.

8. The sample analysis system of claim 7, comprising a chamber positioned to receive droplets emitted from the sample introduction device, and optics between the chamber and the analytical instrument.

9. A method for generating droplets for analysis, the method comprising:
flowing a linear segmented sample array along a sample path through a first tube and out from a first tube outlet, the linear segmented sample array comprising a plurality of first plugs alternately separated by a plurality of second plugs, wherein the first plugs comprise a first fluid and analytes and the second plugs comprise a second fluid different from the first fluid;
flowing a gas along a gas path between the first tube and a second tube surrounding the first tube, and toward a second tube outlet, wherein the sample path merges into the gas path downstream of the first tube outlet such that at least the first plugs are broken into droplets comprising the analytes, and wherein the first tube and the second tube extend along a longitudinal axis, and the second tube outlet is positioned at a downstream axial distance from the first tube outlet; and
emitting a stream of the droplets from the second tube outlet.

10. The method of claim 9, wherein the first fluid and the second fluid have a configuration selected from the group consisting of:
the first fluid and second fluid are substantially immiscible;
one of the first fluid and the second fluid comprises an aqueous medium and other of the first fluid and the second fluid comprises an organic medium; and
the first fluid comprises an aqueous medium and the second fluid comprises a fluorocarbon, an oil, or a gas.

11. The method of claim 9, comprising, before flowing the linear segmented sample array through the first tube, flowing the linear segmented sample array into a sample container, and further comprising at least one of: storing the sample container for a period of time; transporting the sample container to the first tube; or coupling the sample container with the first tube.

12. The method of claim 9, comprising forming the linear segmented sample array.

13. The method of claim 12, comprising, before or after forming the linear segmented sample array, carrying out a sample process on the first fluid selected from the group consisting of:
   mixing the first fluid with another fluid;
   adding a reagent to the first fluid;
   carrying out an analytical separation technique on the first fluid;
   diluting the first fluid;
   carrying out dialysis on the first fluid;
   lysing a cell contained in the first fluid;
   filtering the first fluid;
   transferring heat to or from the first fluid; and
   a combination of two or more of the foregoing.

14. The method of claim 12, wherein forming the linear segmented sample array comprises a step selected from the group consisting of:
   flowing the first fluid from a reservoir;
   flowing the first fluid and the second fluid into a fluid junction, and flowing the linear segmented sample array out from the fluid junction;
   flowing at least one of the first fluid and the second fluid is done according to a pulse sequence; and
   alternately inserting an aspiration tube into a container and aspirating a quantity of at least one of the first fluid and the second fluid from the container, and removing the aspiration tube from the container.

15. The method of claim 9, comprising, before flowing the linear segmented sample array through the first tube, performing a step selected from the group consisting of:
   carrying out liquid-liquid extraction on the linear segmented sample array;
   flowing the linear segmented sample array through a transfer conduit for a period of time sufficient for a component contained in the first plugs or the second plugs to be transferred into adjacent plugs; and
   flowing the linear segmented sample array through a transfer conduit for a period of time sufficient for the first plugs to at least partially merge with the second plugs.

16. A method for ionizing a sample, comprising:
generating droplets according to the method of claim 9;
emitting the droplets into a chamber at about atmospheric pressure; and
ionizing the analytes contained in the droplets.

17. A method for analyzing a sample, comprising:
ionizing analytes according to the method of claim 16 to produce ions; and
measuring an attribute of the ions.

18. A method for atomizing a sample, comprising:
generating droplets according to the method of claim 9;
generating plasma; and
emitting the droplets into the plasma.

19. A method for analyzing a sample, comprising:
atomizing the sample according to the method of claim 18 to produce sample atoms; and
measuring an attribute of the sample atoms or photons emitted from the sample atoms.

20. A method for analyzing a sample, comprising:
producing droplets according to the method of claim 9; and
acquiring data from the analytes contained in the droplets.

* * * * *